United States Patent [19]

Cheng et al.

[11] 4,298,482

[45] Nov. 3, 1981

[54] LOW TEMPERATURE PROCESS OF PREPARING Mg(OH)$_2$ SUSPENSIONS

[75] Inventors: William J. Cheng; David B. Guthrie, both of St. Louis, Mo.

[73] Assignee: Petrolite Corporation, St. Louis, Mo.

[21] Appl. No.: 50,383

[22] Filed: Jun. 20, 1979

[51] Int. Cl.$^3$ .................. C10M 1/10; C10M 3/02; C10M 5/02; C10M 7/02
[52] U.S. Cl. ................................. 252/25; 44/51; 44/66; 44/DIG. 3; 252/18; 252/387
[58] Field of Search ............... 252/18, 25, 387; 44/51, 44/DIG. 3, 66

[56] References Cited

U.S. PATENT DOCUMENTS

| | | | |
|---|---|---|---|
| 2,671,758 | 3/1954 | Vinograd et al. | 252/18 |
| 3,055,829 | 9/1962 | Wiley et al. | 252/18 |
| 3,111,381 | 11/1963 | Panzer et al. | 252/25 |
| 3,523,767 | 8/1970 | McCord | 44/51 |

Primary Examiner—Delbert E. Gantz
Assistant Examiner—Irving Vaughn
Attorney, Agent, or Firm—Sidney B. Ring; Hyman F. Glass

[57] ABSTRACT

This invention relates to a process of preparing stable suspensions of Mg(OH)$_2$ which comprises blending Mg(OH)$_2$ powder with acid in a surfactant-containing fluid to effect particle size reduction of the starting Mg(OH)$_2$ powder. In practice, the mole-fraction of acid employed is less than 50% of that stoichiometrically necessary for the formation of the magnesium salt.

14 Claims, No Drawings

LOW TEMPERATURE PROCESS OF PREPARING Mg(OH)$_2$ SUSPENSIONS

It is difficult to prepare commercial slurries of Mg(OH)$_2$ powder in oil because they readily separate upon standing and then become difficult to resuspend because of severe caking of the settled-out solids.

Therefore, it is presently more commercially advantageous to manufacture the oil-soluble types of magnesium compositions because of the dependability that such suspensions in oil are stable rather than attempt the commercialization of magnesium-containing slurries which prior to this invention are unstable.

For example, suspensions of magnesium-containing compounds have been heretofore prepared by various methods. One such method, which involves the reaction of Mg metal with an alcohol to form an intermediate magnesium alkoxide, is a complicated multi-stepped process. The following are illustrative:

U.S. Pat. Nos. 2,570,058; 2,582,254; 2,593,314; 2,692,239; 2,788,325; 2,834,662; 2,895,913; 2,939,808; 3,018,172; 3,150,089.

Belgian Pat. No. 842,131

Ulric B. Bray, Charles R. Dickey and Vanderveer Voorhees Ind. Eng. Chem., Prod. Res. Dev., 14, 295-8 (1975).

Other processes employing Mg(OH)$_2$ powder, although not considered commercially suitable by Bray, Dickey and Voorhees (loc. cit.), are illustrated by the following:

U.S. Pat. Nos. 3,018,172; 3,524,814; 3,629,109; 3,865,737; 3,928,216.

Belgian Pat. No. 817,035.

Netherlands Application No. 6,410,242.

Application Ser. No. 816,626 filed July 18, 1977, U.S. Pat. No. 4,229,309, disclosed and claims a facile method of preparing stable, fluid magnesium-containing dispersions which comprise heating Mg(OH)$_2$ above its dehydration temperature in the presence of a fluid of low volatility containing a dispersing agent soluble in said fluid.

The process of Ser. No. 816,626, in essence, comprises an almost "explosive" dehydration of magnesium hydroxide to magnesia according to the equation $$Mg(OH)_2 \rightarrow MgO + H_2O.$$

During this dehydration, Mg(OH)$_2$ is disintegrated into minute particles of MgO which are immediately suspended and become stabilized in the fluid by the presence of a dispersing agent.

In Ser. No. 840,192 filed Oct. 17, 1977, now U.S. Pat. No. 4,163,728, issued Aug. 7, 1979 magnesium salts of carboxylic acids (magnesium carboxylates) in a dispersant-containing fluid are also "explosively" decomposed to magnesia. During this decomposition, the magnesium carboxylate is disintegrated into minute particles of MgO which are immediately suspended and stabilized in the fluid by the presence of a dispersing agent.

However, it is to be noted that a stoichiometric amount of carboxylic acids, based on Mg(OH)$_2$, or equivalent, is employed in forming magnesium carboxylates in Ser. No. 840,192.

Ser. No. 853,600 filed Nov. 21, 1977 now U.S. Pat. No. 4,163,728, issued Aug. 7, 1979 teaches that the process of Ser. No. 840,192 can be effectively carried out employing less than stoichiometric amounts of the carboxylic acid. For example, the process can be carried out employing minor percentages of the calculated stoichiometric amounts of carboxylic acid such as less than about 50%, such as about 10% or even 5% or less of the stoichiometric amounts of carboxylic acid. However, despite the fact that such minor stoichiometric amounts of carboxylic acids are employed, the yields of dispersed MgO are substantially the same as achieved by employing stoichiometric amounts of carboxylic acids and greater than that achieved without such minor amounts of carboxylic acid unless the temperature is substantially higher.

Apart from the fact that a low stoichiometry of carboxylic acid is employed in Ser. No. 853,600, the reaction conditions and dispersion-forming temperature ranges in particular are essentially the same as in Ser. No. 840,192.

Ser. No. 885,150 filed Mar. 10, 1978 U.S. Pat. No. 4,226,739, relates to a method of preparing stable, fluid magnesium-containing dispersions which comprises heating MgCO$_3$ in the presence of a fluid of low volatility containing a dispersing agent soluble in the fluid to effect its decomposition into MgO and CO$_2$ at temperatures substantially lower than required when MgCO$_3$ in the dry state is decomposed into the aforesaid products.

We have now discovered a low-cost, practical and energy efficient method of preparing non-settling suspensions of Mg(OH)$_2$ which comprises blending Mg(OH)$_2$ powder and acids in a surfactant-containing hydrocarbon and which method now makes unnecessary the formation of oil-soluble magnesium compounds for many applications. In practice the mole-fraction of acid employed is less than 50% of that stoichiometrically necessary for the formation of magnesium salts. It is unexpected that the product of this invention is stable in view of the fact that, in the absence of acid, the Mg(OH)$_2$ powder employed in the same process, even with the aid of surfactants, is difficult to suspend without separation. Although we do not wish to be bound by theory, it is believed that the magnesium salt initially formed in situ is sub-micron in size and quickly erodes the large particles of Mg(OH)$_2$ powder into smaller particles until equilibration is reached among the species Mg$^{++}$, Mg(OH)$_2$ and acid anion, thus resulting in the easy and lasting suspendability of Mg(OH)$_2$ by the surfactant(s).

It is to be noted that, although the following patent applications:

Ser. No. 816,626 filed July 18, 1977;
Ser. No. 840,192 filed Oct. 17, 1977;
Ser. No. 853,600 filed Nov. 21, 1977;
Ser. No. 885,150 filed Mar. 10, 1978.

relate to the preparation of oil-soluble magnesium overbased compositions, they involve the use of high processing temperatures. The present low temperature process uses less time and energy in addition to other obvious differences.

In addition the present process is substantially different from U.S. Pat. No. 3,523,767 which is summarized in claim 1 thereof:

"1. An oil soluble fuel oil additive characterized by improved stability and pumpability for use in reducing the corrosive effects of contaminants present in residual type fuel oils during the burning thereof, said additive made from the steps comprising, providing an aqueous phase comprising an aqueous slurry of magnesium hydrate containing finely divided, oil insoluble magnesium hydroxide particles, dissolving a long chain fatty acid containing at least six (6) carbon atoms in a hydrocarbon oil solvent and in an amount sufficient to react substantially only with the surfaces of said particles, adding to the acid in solvent mixture a neutralizer selected from the group consisting of ammonia and amine to produce in the solvent an oil soluble soap of said fatty acid, blending together the mixture of soap in said solvent and said magnesium hydrate slurry to react said soap substantially only with the said surfaces of said particles thereby to enable said particles to separate-substantially free of water-from said slurry and into said solvent, and then separating the particles in the solvent from said aqueous phase to produce magnesium hydrate, in situ, in said solvent to give said additive for use with said residual type fuels."

Since a low stoichiometric amount of acid is employed, the product of this invention is in essence a mixture of magnesium salts and magnesium hydroxide of very small particle size.

Any suitable acid at low stoichiometry can be employed to effect the equilibration necessary for particle size reduction of $Mg(OH)_2$. These include mono- and polycarboxylic acids including aliphatic, aromatic, cycloaliphatic, etc., carboxylic acids and mineral acids. Representative examples include: formic acid, acetic acid, propionic acid, butyric acid, acrylic acid, maleic acid, lauric acid, oleic acid, stearic acid, naphthenic acid, benzenesulfonic acid, toluenesulfonic acid, hydrochloric acid, hydrobromic acid, hydroiodic acid, nitric acid, sulfuric acid, etc. The preferred organic acids, i.e., those of the formula

where R is aliphatic, preferably alkyl, such as those of the formula

where n is about 0-17, such as about 0-5 but preferably 1, namely, acetic acid. The preferred mineral acids are, namely, hydrochloric acid, nitric acid, and sulfuric acid.

Any suitable non-volatile process fluid mixture can be employed. The process fluid should be relatively stable and relatively non-volatile. However, any volatility encountered is readily controlled by refluxing and condensing apparatus.

Examples of such non-volatile process fluids are as follows: hydrocarbons (such as kerosene, mineral oil, paraffin oil, or aromatic oil), diphenyl oxide fluids, silicone oils, polyglycol ethers or vegetable oils, etc., or any combinations thereof.

The non-volatile process fluid should contain a dispersant(s) capable of retaining the magnesium compound formed by particle size reduction in stable suspension. Any suitable oil soluble dispersant can be employed.

These are illustrated by the following: saturated and unsaturated fatty acids (such as stearic acid and oleic acid) and derivatives thereof (such as sorbitan monooleate), sulfonic acids (such as mahogany or petroleum derived sulfonic acids and synthetic sulfonic acids), naphthenic acids, oxyalkylated fatty amines, alkylphenols sulfurized alkylphenols, oxyalkylated alkylphenols, etc.

The particle size of the resulting $Mg(OH)_2$ so formed in general should be of a size which is readily suspended and which is capable of becoming a lasting, fluid suspension by the dispersant(s).

The concentration of the magnesium hydroxide particles so formed in the non-volatile process fluid should be no greater than that concentration which maintains suitable fluidity. In general, the final concentration based on non-volatile fluid and other materials is from about 1% to 32% when calculated as percent magnesium, such as from about 2% to 29%, for example, from about 3% to 26%, but preferably from about 4% to 23%.

The concentration of the dispersant(s) in the non-volatile process fluid should be sufficient to maintain a fluid, stable suspension of magnesium hydroxide in the fluid. In general the weight concentrations of dispersant and non-volatile fluid may range from 100% dispersant and 0% non-volatile fluid to as little as 0.01% dispersant and 99.99% fluid, such as from about 95% and 5%, for example from about 90% to 10%, but preferably from about 85 to 15%.

The magnesium hydroxide suspensions of this invention can be further reacted to form suspensions of the corresponding derivatives. For example, after particle size reduction of $Mg(OH)_2$ by equilibration with acids in accord with this invention, the $Mg(OH)_2$ suspensions can be further reacted with $CO_2$ to form $MgCO_3$ suspensions.

The compositions of this invention have a wide variety of uses. The following are illustrative:

1. As a combination anti-corrosion and acidic neutralization additive for lubricating oils and greases.

2. As a combination anti-corrosion and acidic neutralization additive during the combustion of fuels such as residual fuel, pulverized sulfur-containing coal, or mixtures thereof.

3. As a combination anti-weathering and sealing agent for water-proofing cement, concrete, and asphaltic surfaces.

4. In proprietary pharmaceutical and cosmetic formulations.

5. As corrosion inhibitors, particularly in fuels containing vanadium.

The following examples are presented for purposes of illustration and not of limitation.

EXAMPLE 1

(a typical suspension procedure)

To a 4-liter beaker are charged 1890 g kerosene, 94 g (about 0.3 equiv.) dodecylbenzenesulfonic acid and 64 g (about 1.067 mole) glacial acetic acid. The contents are stirred until homogeneous. With stirrer on, 1250 g (about 21.44 moles) magnesium hydroxide is added followed by 218 g kerosene and 154 g sorbitan monooleate. A magnesium sulfonate and magnesium acetate are formed in situ. The mass is stirred for three hours. The viscosity of the mass is about 5000 cps. The magnesium content is calculated at about 14.2% for 3670 g total suspension. There was no separation of layers after 4 months of standing.

EXAMPLE 2

(Preparation of a magnesium sulfonate dispersant)

To a reactor were charged 94 g (about 0.3 equiv.) dodecylbenzenesulfonic acid, 1890 g kerosene and 10 g (about 0.17 mole) of $Mg(OH)_2$. The contents were stirred and heated to 170° C. with the reactor closed, pressure rising to 32 psig. The contents were cooled and drained; net weight was 1985 g. The magnesium content of this product was calculated at 0.21%.

When acetic acid is not used in preparing the suspension, the stability of the suspension, as shown in Example 3, is virtually non-existent.

EXAMPLE 3

To a quart jar were added 400 g magnesium dodecylbenzenesulfonate of Example 2 and 30.8 g sorbitan mono-oleate. The contents were stirred to which was added 248 g $Mg(OH)_2$, Stirring was continued for one hour. The mass was uniform in appearance; but, after one hour of settling, $\frac{1}{3}$ of the kerosene charged had separated as an upper layer.

When acetic is employed in preparing the suspension, the stability of the suspension, as shown in Examples 4 and 5, is astonishingly long-lasting.

EXAMPLE 4

To a quart jar were added 400 g magnesium dodecylbenzenesulfonate of Example 2, 31 g sorbitan mono-oleate and 13 g acetic acid. The contents were stirred to which was added 248 g $Mg(OH)_2$. The contents were stirred for three hours. The mass was allowed to stand for $3\frac{1}{2}$ months. There was virtually no separation of an upper kerosene layer nor a lower solid layer of $Mg(OH)_2$. The magnesium content was calculated at 15.06%.

The long-term stability of the product of Example 4, even when greatly diluted in kerosene fuel, is shown in Example 5.

EXAMPLE 5

The product of Example 4 (2.0 g) was dispersed in kerosene (248 ml) in a 250 ml graduated cylinder. The dispersion (calculated at about 1500 ppm Mg) was then allowed to settle for $3\frac{1}{2}$ months. The upper 10% (25 ml) was removed and analyzed for magnesium content using dry ash/atomic absorption spectroscopy; the Mg content found was 770 ppm or 0.08%. The bottom 3% (7-8 ml) was removed and analyzed; the Mg content found was 757 ppm or 0.08%. This data indicates that about 50% of the $Mg(OH)_2$ had remained suspended over a $3\frac{1}{2}$ month period.

EXAMPLE 6

The product of the procedure of Example 1 where hydrochloric acid is used in place of the molar equivalent of acetic acid.

EXAMPLE 7

The product of the procedure of Example 1 where nitric acid is used in place of the molar equivalent of acetic acid.

EXAMPLE 8

The product of the procedure of Example 1 where sulfuric acid is used in place of $\frac{1}{2}$ of the molar equivalent of acetic acid.

We claim:

1. A process of preparing stable suspensions of $Mg(OH)_2$ which comprises blending at low or ambient temperatures $Mg(OH)_2$ powder with less than a stoichiometric amount of an acid in a relatively non-volatile, relatively stable fluid containing a dispersant which is oil soluble and which is capable of retaining the magnesium compound formed by particle size reduction in stable suspension so as to effect a reduction of the size of the particles of the starting $Mg(OH)_2$ powder to a size which is readily suspended and which is capable of becoming a lasting, fluid suspension, the total amount of acid present as a reactant and as the dispersant being less than the stoichiometric amount of acid required to react with the $Mg(OH)_2$ powder.

2. The process of claim 1 where the acid is a carboxylic acid.

3. The process of claim 2 where the carboxylic acid is acetic acid.

4. The process of claim 1 where the acid is an inorganic acid.

5. The process of claim 4 where the inorganic acid is hydrochloric acid.

6. The process of claim 4 where the inorganic acid is nitric acid.

7. The process of claim 4 where the inorganic acid is sulfuric acid.

8. The process of claim 1 where less than 50% of the acid stoichiometrically necessary for the formation of magnesium salts is employed.

9. The process of claim 2 where less than 50% of the acid stoichiometrically necessary for the formation of magnesium salts is employed.

10. The process of claim 3 where less than 50% of the acid stoichiometrically necessary for the formation of magnesium salts is employed.

11. The process of claim 4 where less than 50% of the acid stoichiometrically necessary for the formation of magnesium salts is employed.

12. The process of claim 5 where less than 50% of the acid stoichiometrically necessary for the formation of magnesium salts is employed.

13. The process of claim 6 where less than 50% of the acid stoichiometrically necessary for the formation of magnesium salts is employed.

14. The process of claim 7 where less than 50% of the acid stoichiometrically necessary for the formation of magnesium salts is employed.

* * * * *